US012486535B2

(12) United States Patent
Ortogero et al.

(10) Patent No.: US 12,486,535 B2
(45) Date of Patent: Dec. 2, 2025

(54) ECTOPIC PREGNANCY KITS AND METHODS

(71) Applicant: The Government of the United States, as Represented by the Secretary of the Army, Fort Detrick, MD (US)

(72) Inventors: Nicole E. Ortogero, Kent, WA (US); Richard O. Burney, University Place, WA (US); Gregory E. Chow, University Place, WA (US); Jessica Lentscher, Lakewood, WA (US); Zachary Colburn, Lakewood, WA (US)

(73) Assignee: THE GOVERNMENT OF THE UNITED STATES, AS REPRESENTED BY THE SECRETARY OF THE ARMY, Frederick, MD (US)

( * ) Notice: Subject to any disclaimer, the term of this patent is extended or adjusted under 35 U.S.C. 154(b) by 1264 days.

(21) Appl. No.: 16/293,415

(22) Filed: Mar. 5, 2019

(65) Prior Publication Data

US 2019/0390272 A1 Dec. 26, 2019

Related U.S. Application Data

(60) Provisional application No. 62/638,415, filed on Mar. 5, 2018.

(51) Int. Cl.
*C12Q 1/68* (2018.01)
*C12Q 1/6876* (2018.01)

(52) U.S. Cl.
CPC ...... *C12Q 1/6876* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

2010/0285974 A1* 11/2010 Horne .................. C12Q 1/6883 435/7.1
2015/0031616 A1* 1/2015 Conrad ................ C12Q 1/6876 514/12.7

OTHER PUBLICATIONS

Lozeau et al; Am Fam Physician 2005, 72, pp. 1707-1714.*
Duncan et al; PLOS One; 6(8); e23595; 2011; pp. 1-11.*
Li et al; Combinatorial Chemistry & High Throughput screening; 2001, pp. 727-739, vol. 4.*
Affymetrix (Affymetrix, Gene Chip 2.0 ST array).*

* cited by examiner

*Primary Examiner* — Jehanne S Sitton
(74) *Attorney, Agent, or Firm* — Leigh Z. Callander

(57) ABSTRACT

The disclosure generally provides methods for early detection of ectopic pregnancy, and utilization of endometrial molecular signatures. This disclosure more specifically relates to gene sets that, in aggregate, reliably classify the location of a nonviable pregnancy as intrauterine or ectopic and can identify a patient for therapeutic intervention. The disclosure also illustrates cilia-associated genes as a classifier for ectopic pregnancy with high accuracy for delineating ectopic from intrauterine pregnancies.

22 Claims, 10 Drawing Sheets

Specification includes a Sequence Listing.

FIGURE 2

List of cilia-associated genes differentially expressed in ectopic pregnancy endometrial biopsies.

| Gene Name | Gene Symbol | ENSEMBL Accession | HPA Tissue Expression |
|---|---|---|---|
| Armadillo repeat containing 3 | *ARMC3* | ENSG00000165309 | Fallopian tube and testis enriched |
| Chromosome 20 open reading frame 85 | *C20orf85* | ENSG00000124237 | Fallopian tube enriched |
| Cilia and flagella associated protein 47 | *CFAP47* | ENSG00000165164 | Fallopian tube enriched |
| Cilia and flagella associated protein 126 | *CFAP126* | ENSG00000188931 | Fallopian tube enriched |
| Dynein axonemal heavy chain 12 | *DNAH12* | ENSG00000174844 | Fallopian tube and testis enriched |
| Leucine rich repeat containing 46 | *LRRC46* | ENSG00000141294 | Fallopian tube and testis enriched |
| Lysophosphatidic acid receptor 3 | *LPAR3* | ENSG00000171517 | Fallopian tube enriched |
| Radial spoke head 4 homolog A | *RSPH4A* | ENSG00000111834 | Fallopian tube enriched |
| Stomatin like 3 | *STOML3* | ENSG00000133115 | Fallopian tube enriched |
| Tubulin polymerization promoting protein family member 3 | *TPPP3* | ENSG00000159713 | Fallopian tube enriched |
| WD repeat domain 49 | *WDR49* | ENSG00000174776 | Fallopian tube enriched |
| Zinc finger B-box domain containing | *ZBBX* | ENSG00000169064 | Fallopian tube and testis enriched |

FIGURE 3

Patient characteristics.

| Characteristic | Average (Range) | | | | p-value |
|---|---|---|---|---|---|
| | AIUP (n = 9) | | ECT (n = 8) | | |
| Age | 26.7 | (20 – 38) | 33.0 | (28 – 38) | 0.06 |
| Body Mass Index | 25.4 | (22.3 – 27.3) | 25.6 | (20.0 – 32.0) | 0.92 |
| Gravidity | 2.4 | (1 – 4) | 2.9 | (1 – 5) | 0.55 |
| Estimated Gestational Age (Days) | 58.6 | (50 – 66) | 44.8 | (37 – 54) | <0.05 |
| Serum Progesterone (ng/mL) | 6.5 | (1.8 – 13.9) | 7.5 | (0.7 – 15.0) | 0.84 |

FIGURE 4 qPCR Primer Sequences.

| Gene | Forward | | Reverse | |
|---|---|---|---|---|
| *C20orf85* | GGTGACCCCAGTGGAGAAG | SEQ ID NO: 1 | TCGAGCTCTAGGCACTTGTTC | SEQ ID NO: 2 |
| *CFAP47* | TGAACCTGCAAAGGGAAACTT | SEQ ID NO: 3 | CCTTTTCCAGAGACCCATGA | SEQ ID NO: 4 |
| *CFAP126* | GCCAACGATCGTGGTCAT | SEQ ID NO: 5 | GAAGGAACCCCAAGGATTTG | SEQ ID NO: 6 |
| *LPAR3* | AGCTAATGAAGACGGTGATGACT | SEQ ID NO: 7 | CACCTTTTCACATGCTGCAC | SEQ ID NO: 8 |
| *LRRC46* | AGTGGCCCATTCTGCTCA | SEQ ID NO: 9 | CTGTCAGGGCCGTCTGTT | SEQ ID NO: 10 |
| *RPL19* | TCAAAAACAAGCGGATTCTCA | SEQ ID NO: 11 | GCGTGCTTCCTTGGTCTTAG | SEQ ID NO: 12 |
| *STOML3* | CGTGCAGTTGCAGAGATCC | SEQ ID NO: 13 | GGGAGACTCAGCCAGCAC | SEQ ID NO: 14 |
| *WDR49* | GTGAGCCAGGTGGTCAGTTAC | SEQ ID NO: 15 | TCAATATGCCAGTGCTTTGC | SEQ ID NO: 16 |

FIGURE 5

Differentially expressed genes.

| PROBEID | ENSEMBL | SYMBOL | GENENAME | $log_2FC$ | P.Value | adj.P.Val |
|---|---|---|---|---|---|---|
| 16885819 | ENSG00000244337 | *AJ239322.3* | AJ239322.3 | -0.70 | 0.000 | 0.091 |
| 16703182 | ENSG00000165309 | *ARMC3* | armadillo repeat containing 3 | 0.87 | 0.000 | 0.059 |
| 16915213 | ENSG00000124237 | *C20orf85* | chromosome 20 open reading frame 85 | 1.10 | 0.000 | 0.059 |
| 16695690 | ENSG00000188931 | *CFAP126* | cilia and flagella associated protein 126 | 1.28 | 0.000 | 0.059 |
| 17102483 | ENSG00000165164 | *CFAP47* | cilia and flagella associated protein 47 | 0.85 | 0.000 | 0.059 |
| 16828471 | ENSG00000183196 | *CHST6* | carbohydrate sulfotransferase 6 | 0.76 | 0.000 | 0.091 |
| 16857748 | ENSG00000104938 | *CLEC4M* | C-type lectin domain family 4 member M | -1.08 | 0.000 | 0.073 |
| 17021504 | ENSG00000118432 | *CNR1* | cannabinoid receptor 1 | -2.75 | 0.000 | 0.060 |
| 16888610 | ENSG00000168542 | *COL3A1* | collagen type III alpha 1 chain | 0.85 | 0.000 | 0.059 |
| 16955368 | ENSG00000174844 | *DNAH12* | dynein axonemal heavy chain 12 | 0.78 | 0.000 | 0.068 |
| 17004612 | ENSG00000096696 | *DSP* | desmoplakin | 0.83 | 0.000 | 0.068 |
| 17040037 | ENSG00000231389 | *HLA-DPA1* | major histocompatibility complex, class II, DP alpha 1 | -0.57 | 0.000 | 0.059 |
| 16717342 | ENSG00000172987 | *HPSE2* | heparanase 2 (inactive) | 1.17 | 0.000 | 0.059 |
| 17106242 | ENSG00000260802 | *LINC00890* | long intergenic non-protein coding RNA 890 | -1.76 | 0.000 | 0.069 |
| 16688992 | ENSG00000171517 | *LPAR3* | lysophosphatidic acid receptor 3 | 0.77 | 0.000 | 0.059 |
| 16835322 | ENSG00000141294 | *LRRC46* | leucine rich repeat containing 46 | 0.67 | 0.000 | 0.059 |
| 16725306 | ENSG00000166959 | *MS4A8* | membrane spanning 4-domains A8 | 1.24 | 0.000 | 0.091 |
| 17095882 | ENSG00000127083 | *OMD* | osteomodulin | -1.55 | 0.000 | 0.073 |
| 16843156 | ENSG00000126861 | *OMG* | oligodendrocyte myelin glycoprotein | 1.19 | 0.000 | 0.073 |
| 16669180 | ENSG00000134247 | *PTGFRN* | prostaglandin F2 receptor inhibitor | 0.77 | 0.000 | 0.091 |
| 16920156 | ENSG00000124212 | *PTGIS* | prostaglandin I2 synthase | -0.83 | 0.000 | 0.059 |
| 16906991 | ENSG00000162944 | *RFTN2* | raftlin family member 2 | 0.82 | 0.000 | 0.059 |
| 16700341 | ENSG00000199672 | *RNU4-21P* | RNA, U4 small nuclear 21, pseudogene | -0.80 | 0.000 | 0.059 |
| 16942797 | ENSG00000240241 | *RP11-314M24.1* | RP11-314M24.1 | 1.55 | 0.000 | 0.059 |
| 17011980 | ENSG00000111834 | *RSPH4A* | radial spoke head 4 homolog A | 0.96 | 0.000 | 0.059 |
| 17079434 | ENSG00000207067 | *SNORA72* | small nucleolar RNA, H/ACA box 72 | -1.40 | 0.000 | 0.059 |
| 16716795 | ENSG00000095637 | *SORBS1* | sorbin and SH3 domain containing 1 | -0.91 | 0.000 | 0.068 |
| 16977833 | ENSG00000152583 | *SPARCL1* | SPARC like 1 | -0.52 | 0.000 | 0.059 |
| 16778313 | ENSG00000133115 | *STOML3* | stomatin like 3 | 0.63 | 0.000 | 0.059 |
| 16827344 | ENSG00000159713 | *TPPP3* | tubulin polymerization promoting protein family member 3 | 0.63 | 0.000 | 0.068 |
| 16704767 | ENSG00000283652 | *WDFY4* | WDFY family member 4 | -0.68 | 0.000 | 0.091 |
| 16961250 | ENSG00000174776 | *WDR49* | WD repeat domain 49 | 0.90 | 0.000 | 0.059 |
| 16999927 | ENSG00000199677 | *Y_RNA.58-201* | Y_RNA.58-201 | -0.78 | 0.000 | 0.097 |
| 16961200 | ENSG00000169064 | *ZBBX* | zinc finger B-box domain containing | 1.03 | 0.000 | 0.059 |

SEQUENCE LISTING

<160> NUMBER OF SEQ ID NOS: 16

<210> SEQ ID NO 1
<211> LENGTH: 19
<212> TYPE: DNA
<213> ORGANISM: Artificial Sequence
<220> FEATURE:
<223> OTHER INFORMATION: primer sequence

<400> SEQUENCE: 1
ggtgacccca gtggagaag 19

<210> SEQ ID NO 2
<211> LENGTH: 21
<212> TYPE: DNA
<213> ORGANISM: Artificial Sequence
<220> FEATURE:
<223> OTHER INFORMATION: primer sequence

<400> SEQUENCE: 2
tcgagctcta ggcacttgtt c 21

<210> SEQ ID NO 3
<211> LENGTH: 21
<212> TYPE: DNA
<213> ORGANISM: Artificial Sequence
<220> FEATURE:
<223> OTHER INFORMATION: primer sequence

<400> SEQUENCE: 3
tgaacctgca aagggaaact t 21

<210> SEQ ID NO 4
<211> LENGTH: 20
<212> TYPE: DNA
<213> ORGANISM: Artificial Sequence
<220> FEATURE:
<223> OTHER INFORMATION: primer sequence

<400> SEQUENCE: 4
ccttttccag agacccatga 20

<210> SEQ ID NO 5
<211> LENGTH: 18
<212> TYPE: DNA
<213> ORGANISM: Artificial Sequence
<220> FEATURE:
<223> OTHER INFORMATION: primer sequence

<400> SEQUENCE: 5
gccaacgatc gtggtcat 18

<210> SEQ ID NO 6
<211> LENGTH: 20
<212> TYPE: DNA
<213> ORGANISM: Artificial Sequence
<220> FEATURE:
<223> OTHER INFORMATION: primer sequence

<400> SEQUENCE: 6
gaaggaaccc caaggatttg 20

<210> SEQ ID NO 7
<211> LENGTH: 23
<212> TYPE: DNA
<213> ORGANISM: Artificial Sequence
<220> FEATURE:
<223> OTHER INFORMATION: primer sequence

<400> SEQUENCE: 7
agctaatgaa gacggtgatg act 23

<210> SEQ ID NO 8
<211> LENGTH: 20
<212> TYPE: DNA
<213> ORGANISM: Artificial Sequence
<220> FEATURE:
<223> OTHER INFORMATION: primer sequence

<400> SEQUENCE: 8
caccttttca catgctgcac 20

<210> SEQ ID NO 9
<211> LENGTH: 18
<212> TYPE: DNA
<213> ORGANISM: Artificial Sequence
<220> FEATURE:
<223> OTHER INFORMATION: primer sequence

<400> SEQUENCE: 9
agtggcccat tctgctca 18

<210> SEQ ID NO 10
<211> LENGTH: 18
<212> TYPE: DNA
<213> ORGANISM: Artificial Sequence
<220> FEATURE:
<223> OTHER INFORMATION: primer sequence

<400> SEQUENCE: 10
ctgtcagggc cgtctgtt 18

<210> SEQ ID NO 11
<211> LENGTH: 21
<212> TYPE: DNA
<213> ORGANISM: Artificial Sequence
<220> FEATURE:
<223> OTHER INFORMATION: primer sequence

<400> SEQUENCE: 11
tcaaaaacaa gcggattctc a 21

<210> SEQ ID NO 12
<211> LENGTH: 20
<212> TYPE: DNA
<213> ORGANISM: Artificial Sequence
<220> FEATURE:
<223> OTHER INFORMATION: primer sequence

<400> SEQUENCE: 12
gcgtgcttcc ttggtcttag 20

<210> SEQ ID NO 13
<211> LENGTH: 19
<212> TYPE: DNA
<213> ORGANISM: Artificial Sequence
<220> FEATURE:
<223> OTHER INFORMATION: primer sequence

<400> SEQUENCE: 13
cgtgcagttg cagagatcc 19

-continued

```
<210> SEQ ID NO 14
<211> LENGTH: 18
<212> TYPE: DNA
<213> ORGANISM: Artificial Sequence
<220> FEATURE:
<223> OTHER INFORMATION: primer sequence

<400> SEQUENCE: 14

gggagactca gccagcac                                                18


<210> SEQ ID NO 15
<211> LENGTH: 21
<212> TYPE: DNA
<213> ORGANISM: Artificial Sequence
<220> FEATURE:
<223> OTHER INFORMATION: primer sequence

<400> SEQUENCE: 15

gtgagccagg tggtcagtta c                                            21


<210> SEQ ID NO 16
<211> LENGTH: 20
<212> TYPE: DNA
<213> ORGANISM: Artificial Sequence
<220> FEATURE:
<223> OTHER INFORMATION: primer sequence

<400> SEQUENCE: 16

tcaatatgcc agtgctttgc                                              20
```

ECTOPIC PREGNANCY KITS AND METHODS

GOVERNMENTAL RIGHTS

This invention was made with support from the United States Government and the Madigan Army Medical Center. Accordingly, the United States government has certain rights in this invention. Funding for this work was provided by the Army Medical Department Advanced Medical Technology Initiative (AAMTI).

FIELD

This disclosure generally relates to early detection of ectopic pregnancy, and utilization of endometrial molecular signatures. This disclosure more specifically relates to compositions of matter, kits, gene sets, and methods that improve the timing of a reliable classification of a nonviable intrauterine or ectopic pregnancy.

BACKGROUND

Ectopic pregnancy (ECT) is the leading cause of morbidity and mortality among women in the first trimester. An ectopic pregnancy occurs when implantation of a fertilized ovum occurs outside of the uterine endometrium. Ectopic pregnancy is a common pregnancy outcome, affecting 1-2% of pregnancies in the United States.[2] Most ectopic pregnancies implant within the fallopian tubes (93-98%), with the majority occurring within the ampullae of the fallopian tube.[3]

Ectopic pregnancy can cause catastrophic outcomes for patients, particularly in poor or low access health care systems. Common risk factors include prior fallopian tubal surgery, congenital tubal anomalies, artificial reproductive technologies (ART), previous ectopic pregnancy and a history of pelvic inflammatory disease (PID). Patients may present with vaginal spotting and cramping, but also may be asymptomatic.[3] Current determination and management of ectopic pregnancy relies on the use of a combination of transvaginal ultrasound (TVUS) and human chorionic gonadotropin (hCG). Unfortunately, this requires sufficient trophoblastic proliferation to allow for a definitive diagnosis. In addition, a pregnancy which is not advanced enough to diagnose either intrauterine or ectopic pregnancy is determined to be a pregnancy of unknown location (PUL). Non-viable intrauterine pregnancy (NV-IUP) is defined as a clinically diagnosed pregnancy with β-hCG levels not rising as expected for a normal intrauterine pregnancy or definitive evidence of embryonic arrest. Pregnancies of unknown location (e.g., NV-PUL) may present similarly during the first trimester, with vaginal bleeding/spotting and abdominal cramping, along with abnormally rising β-hCG levels. Distinguishing between these clinical diagnoses is important, as the management and treatment regimen may vary considerably and be determinative saving the patient further morbidity.

Pregnancy of unknown location (PUL) is defined by a positive pregnancy test with no signs of intrauterine pregnancy or an extrauterine pregnancy via transvaginal ultrasound. It is often difficult to determine the location of the pregnancy in cases of PUL. The reported rate of PUL in women seeking early pregnancy care varies between 5 and 42% in the literature and the frequency of PUL appears to be increasing.

The current state of the art lacks a reliable early-stage test for determination of ectopic pregnancy. Further the art lacks any simple and accurate test (e.g., biomarkers) for detecting ectopic pregnancy, or distinguishing and/or identifying PUL from ectopic pregnancy. There is a desperate need in the art for compositions (e.g., kits) and methods that improve clinical management of early stage pregnancy in order to reduce the life-threatening complications that can arise from an ectopic pregnancy. The compositions, kits, and methods disclosed herein provide for an early-stage, reliable test for the determination and identification of ectopic pregnancy in patients having non-viable pregnancy of unknown location (NV-PUL).

SUMMARY OF THE DISCLOSURE

In one aspect, the disclosure provides a method for detecting ectopic pregnancy in a patient, comprising detecting in a biological sample from the patient, differential expression of at least one gene selected from ARMC3; C20orf85; CFAP47; CFAP126; DNAH12; LRRC46; LPAR3; RSPH4A; STOML3; TPPP3; WDR49; and ZBBX, or orthologs thereof, wherein the differential expression of the at least one gene is indicative of ectopic pregnancy. In embodiments of this aspect, the method comprises detecting one, two, three, four, five, six, seven, eight, nine, ten, eleven, or twelve of the cilia-associated genes.

In another aspect, the disclosure provides a method of detecting early stage ectopic pregnancy in a patient, comprising detecting in a biological sample from the patient, differential expression of at least one gene selected from ARMC3; C20orf85; CFAP47; CFAP126; DNAH12; LRRC46; LPAR3; RSPH4A; STOML3; TPPP3; WDR49; and ZBBX, or orthologs thereof, wherein the differential expression of the at least one gene is indicative of early stage ectopic pregnancy. In embodiments of this aspect, the method comprises detecting one, two, three, four, five, six, seven, eight, nine, ten, eleven, or twelve of the cilia-associated genes.

In some embodiments of the above aspects, the method comprises detecting the differential expression of each of the genes ARMC3; C20orf85; CFAP47; CFAP126; DNAH12; LRRC46; LPAR3; RSPH4A; STOML3; TPPP3; WDR49; and ZBBX, or orthologs thereof.

In a further aspect, the disclosure provides a method comprising detecting in a biological sample from a pregnant patient, the differential expression of at least twelve cilia-associated genes comprising ARMC3; C20orf85; CFAP47; CFAP126; DNAH12; LRRC46; LPAR3; RSPH4A; STOML3; TPPP3; WDR49; and ZBBX, or orthologs thereof. In some embodiments of this aspect, the pregnant patient is in the first trimester of pregnancy.

In another aspect, the disclosure provides a method for classifying a pregnancy in a patient, comprising detecting in a biological sample from the patient, the differential expression of at least one cilia-associated gene selected from the group consisting of ARMC3; C20orf85; CFAP47; CFAP126; DNAH12; LRRC46; LPAR3; RSPH4A; STOML3; TPPP3; WDR49; and ZBBX, and orthologs thereof. In embodiments of this aspect, the method comprises detecting one, two, three, four, five, six, seven, eight, nine, ten, eleven, or twelve of the cilia-associated genes. In embodiments of this aspect, the method further comprises detecting the differential expression of each of the genes ARMC3; C20orf85; CFAP47; CFAP126; DNAH12; LRRC46; LPAR3; RSPH4A; STOML3; TPPP3; WDR49; and ZBBX, or orthologs thereof. In further embodiments, the pregnancy is selected from the group consisting of an intrauterine pregnancy, a pregnancy of unknown origin (PUL), a non-viable pregnancy of unknown location (NV-PUL), a non-viable intrauterine pregnancy (NV-IUP), and an ectopic pregnancy (ECT). In yet further embodiments, the pregnancy is an ectopic pregnancy.

In yet another aspect, the disclosure provides a method for distinguishing ectopic pregnancy from abnormal intrauterine pregnancy in a patient, comprising detecting in a biological sample from the patient, the differential expression of at least one cilia-associated gene selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, wherein the differential expression of the at least one gene identifies an ectopic pregnancy. In embodiments of this aspect, the method comprises detecting one, two, three, four, five, six, seven, eight, nine, ten, eleven, or twelve of the cilia-associated genes. In embodiments of this aspect, the method further comprises detecting the differential expression of each of the genes ARMC3; C20orf85; CFAP47; CFAP126; DNAH12; LRRC46; LPAR3; RSPH4A; STOML3; TPPP3; WDR49; and ZBBX, or orthologs thereof.

In another aspect, the disclosure provides a method of treating a patient previously diagnosed with a nonviable first trimester pregnancy, comprising detecting in a biological sample from the patient, differential expression of at least one cilia-associated gene selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, and treating the patient having differential expression of the at least one gene with an emergency surgical intervention. In embodiments of this aspect, the method comprises detecting one, two, three, four, five, six, seven, eight, nine, ten, eleven, or twelve of the cilia-associated genes. In some embodiments of this aspect, the method further comprises detecting the differential expression of each of the genes ARMC3; C20orf85; CFAP47; CFAP126; DNAH12; LRRC46; LPAR3; RSPH4A; STOML3; TPPP3; WDR49; and ZBBX, or orthologs thereof.

In a further aspect, the disclosure provides a method of detecting expression level of a specific set of genes in a biological sample from a pregnant patient who is suspected of having or at risk of having a pregnancy of unknown location, the method comprising quantifying the level of expression of cilia-associated genes comprising: ARMC3; C20orf85; CFAP47; CFAP126; DNAH12; LRRC46; LPAR3; RSPH4A; STOML3; TPPP3; WDR49; and ZBBX, and orthologs thereof. In embodiments of this aspect, the method can further comprise detecting in the sample the expression level of one or more additional genes selected from the group consisting of AJ239322.3, CHST6, CLEC4M, CNR1, COL3A1, DSP, HLA-DPA1, HPSE2, LINC00890, MS4A8, OMD, OMG, PTGFRN, PTGIS, FRFTN2, RNU4-21P, RP11-314M24.1, SNORA72, SORBS1, SPARCL1, WDFY4, and Y_RNA.58-201. In embodiments of this aspect, the method can comprise detecting mRNA, cDNA, or polypeptide.

In embodiments of any of the above aspects, the differential expression detected may be increased relative to a reference expression level.

In any of the above aspects and embodiments the methods may further comprise transvaginal ultrasound (TVUS), or detection of human chorionic gonadotropin (hCG), or both.

In another aspect, the disclosure provides an array comprising at least twelve target oligonucleotides immobilized on a substrate, wherein each target oligonucleotide comprises a unique sequence that is specifically hybridizable to only one of at least twelve separate genes selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, such that the array comprises at least one target oligonucleotide for each of the at least twelve genes. In some embodiments of this aspect, the target oligonucleotides are labelled directly or indirectly with a detectable label. In further embodiments, the detectable label comprises biotin, and further optionally wherein streptavidin-conjugated phycoerythrin (SAPE) is bound to the biotin, or wherein the target oligonucleotide is immobilized on the substrate through binding with a capture probe.

In a further aspect, the disclosure provides an array comprising at least twelve specific binding agents immobilized on a substrate, wherein each specific binding agent specifically binds only one of twelve polypeptides encoded by a gene selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, such that the array comprises at least one specific binding agent for each of the at least twelve polypeptides.

In further aspects, the disclosure provides kits for the diagnosis of ectopic pregnancy.

In some embodiments the kit comprises at least twelve specific binding agents immobilized on a substrate, wherein each specific binding agent specifically binds only one of twelve polypeptides encoded by a gene selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, such that the kit comprises at least one specific binding agent for each of the at least twelve polypeptides.

In some embodiments, the kit comprises at least twelve detectably labelled oligonucleotides, wherein each of the twelve oligonucleotides comprises a unique sequence that is specifically hybridizable to only one of at least twelve separate genes selected from the group consisting of ARMC3; C20orf85; CFAP47; CFAP126; DNAH12; LRRC46; LPAR3; RSPH4A; STOML3; TPPP3; WDR49; and ZBBX, and orthologs thereof, such that the kit comprises at least one target oligonucleotide for each of the at least twelve genes. In the embodiments relating to kits, the kits may also comprise instructions for use.

In some embodiments kits can comprise any type of commercially available detection technology known in the art. For example, kits may comprise a pair of amplification primers which hybridize to the nucleic acid coding for the target cilia-associated gene sequence(s). The primers can comprise a sequence of 6-50, in particular 10-30, 15-30 or 20-30 contiguous nucleotides of the target nucleic acid and are non-overlapping, in order to avoid the formation of primer multimers (e.g., primer dimers). In embodiments, one of the pair of primers will hybridize to one strand of the target sequence, and the other primer will hybridize to the complementary strand in an arrangement which allows amplification of the nucleic acid coding for the cilia-associated gene. In other embodiments the kits may include molecular detection probes, substrates, specific binding agents (e.g., antibodies, specific binding pairs) and reagents that allow the kit to be used with any commercially available detection system.

Other aspects will be apparent to one of skill in the art upon review of the description and exemplary aspects and embodiments that follow.

BRIEF DESCRIPTION OF THE DRAWINGS

The drawings are provided to help illustrate and describe certain features of the aspects and embodiments of the disclosure. However, the claims and disclosure is not limited to the precise arrangements and instrumentalities of the features depicted in the drawings.

FIG. 2 illustrates cilia-associated genes differentially expressed in ectopic pregnancy endometrial biopsies. Gene information for cilia-associated genes used for non-viable pregnancy location classifier. Classifier consists of 12 cilia-associated genes of which all were found to have enriched expression in the fallopian tube based on the Human Protein Atlas (HPA).

FIG. 3 lists key demographics of patients used on study including age body mass index (BMI), gravidity, estimated gestational age (EGA), and serum progesterone (P4). All characteristics except EGA were found to have no statistical difference between NV-IUP and ECT groups.

FIG. 4 shows qPCR Primer sequences. Forward and reverse primer sequences are shown for qPCR validation results.

FIG. 5 shows differentially expressed genes. Results from limma analysis of Affymetrix GeneChip Human Gene 2.0 ST Array comparing ectopic (n=8) and non-viable intrauterine pregnancy endometrial biopsies (n=9). A total of 34 genes were identified as differentially expressed based on a false discovery rate of 10% and log2 fold change of 0.5.

FIG. 9A illustrates tissue expression patterns of differentially expressed genes in log odds by location. Initial results indicated an enrichment of fallopian tube (FT) genes differentially expressed between non-viable intrauterine and ectopic pregnancies. FIG. 9B shows tissue expression patterns of differentially expressed genes as well as initial indication of cilia-associated genes (6 out of 13 cilia initially identified to function in groups FT and FT & Testis upon further investigation 12 out of 12 of the resulting cilia-associated gene classifier were found to be enriched in FT as displayed in FIG. 2).

DETAILED DESCRIPTION

Figure 1:
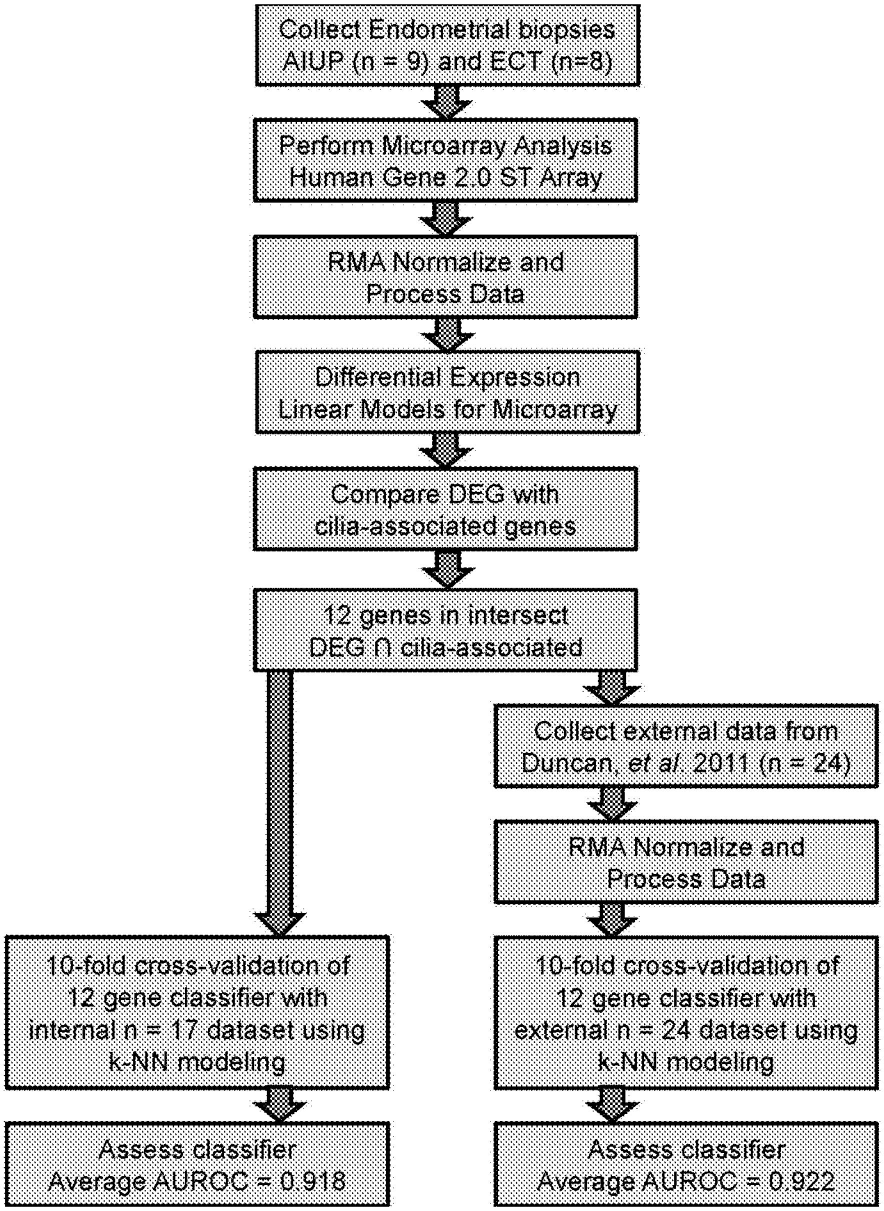
FIG. 1 shows a diagram outlining the steps taken to develop and validate a non-viable pregnancy location classifier. Endometrial biopsies were collected from 17 patients with non-viable intrauterine (NV-IUP) or ectopic (ECT) pregnancies. Samples were analyzed for differential gene expression. Genes were selected based on cilia-association and a classifier was built and tested with the same internal dataset. An external dataset was used for further validation of the accuracy of detection with the cilia-associated gene classifier.

Before continuing to describe various aspects and embodiments in further detail, it is to be understood that this disclosure is not limited to specific compositions or process steps and may vary. As used in this specification and the appended claims, the singular form "a", "an" and "the" include plural referents unless the context clearly dictates otherwise.

Unless defined otherwise, all technical and scientific terms used herein have the same meaning as commonly understood by one of ordinary skill in the art to which this invention is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this invention.

Ectopic pregnancy (ECT) is defined as the implantation of a fertilized ovum outside of the uterus, typically in the Fallopian tube. Ectopic pregnancy accounts for 1 to 2% of all pregnancies in the United States and remains the leading cause of maternal death in the first trimester. The term, pregnancy of unknown location (PUL) is used to describe the diagnostic dilemma in which a positive pregnancy test is obtained, but ultrasound fails to pinpoint the location of the pregnancy as intra- or extrauterine. Nearly 31% of women referred for ultrasound assessment in early pregnancy due to bleeding and/or pelvic pain may be initially classified as having a PUL. Up to 25% of women with ectopic pregnancy will initially be diagnosed with PUL. Currently, when an ultrasound is not definitive of pregnancy location, serial assessment of serum human chorionic gonadotropin (hCG) and/or progesterone is conducted. However, the use of serum hCG and/or progesterone to identify ectopic pregnancy is limited by high false-positive and false negative rates. In women with a PUL, definitive diagnosis can be time consuming and cumbersome, often requiring multiple office visits, serial blood draws, ultrasound examinations, and surgical procedures over a period of time which may span several weeks.

Diagnostic algorithms for diagnosis of early pregnancies are currently limited. The process is often expensive and time-consuming for patients and clinicians. Serial beta human chorionic gonadotrophin (β-hCG) levels, transvaginal ultrasounds, clinic visits, and surgical evaluation may be necessary before a definitive diagnosis is known. During this period of diagnostic delay, women are at risk of tubal rupture and potential death, so time-efficient diagnosis can be lifesaving. [4] Serial measurements of β-hCG have traditionally been used to differentiate viable intrauterine pregnancy from non-viable pregnancies by designating appropriate rates at which HCG increased (24% in 24 hours and 53% at 48 hours). [5] A later study demonstrated a rise of 35% over 48 hours as the minimal rise consistent with a viable pregnancy, as concerns for potential termination of viable pregnancies using a more liberal cut-off were noted. [6][7] The pattern of rise in ECT pregnancies can be misleading for clinicians as well; up to 15-20% of ECT pregnancies will have a β-hCG rise which mimics an intrauterine pregnancy (IUP). [8]

Transvaginal ultrasound (TVUS) is also commonly used to assist in distinguishing an ECT from an IUP. Initially TVUS was used to exclude an IUP; however with advances in imaging resolution, pregnancy can be identified in the adnexa. [3][9] In a large study by Kirk et. al, 5,000 consecutive pregnant patients were scanned, and 120 ultimately were diagnosed with ECT. Using TVUS, clinicians were able make the diagnosis of ECT with a sensitivity of 98.3% prior to confirmation with surgical evaluation. [9] Reasonable proliferation of trophoblastic tissue is requisite to demonstrate this level of sensitivity for diagnosis.

Currently available technologies for identifying an ectopic pregnancy have low accuracy, conflicting detection results, require multiple assays to be performed, and/or cannot reliably distinguish between abnormal intrauterine pregnancies and ectopic pregnancy. Several multiple marker tests have previously been reported but each requires multiple assays. To date, the only markers widely used for ectopic pregnancy are hCG and progesterone. As discussed herein, the inventors have developed a robust assay gene set that can be used to accurately diagnose ectopic pregnancy. No diagnostic links have been previously made between this genomic classifier and ectopic pregnancy. The convenience and accuracy of this classifier would vastly improve upon current clinical measurements, and translates to greater quality and safety in the management of early nonviable pregnancies of unknown location.

Several biomarkers have been previously evaluated to decrease the time required and improve the accuracy in the diagnosis of abnormal pregnancies. A broad range of biomarker candidates for ectopic pregnancy have been proposed, however these have demonstrated variable accuracy and utility. Markers of trophoblastic function have looked at hCG, hyperglycosylated hCG, Activin A, pregnancy-associated plasma protein-A, pregnancy-specific β-glycoprotein 1, placental RNA and human placental lactogen.[4][10] Progesterone, and inhibin A have been evaluated for prediction of pregnancy based on corpus luteum function, however inhibin A has only been reported to have an accuracy of 60%. [4]

In 2012, Home et. al, evaluated a disintegrin and metalloprotease protein-12 (ADAM-12), and found that serum ADAM-12 levels were of limited value in detecting ectopic pregnancy. [11] Previously molecular marker Schwangerschafts protein 1 (SP-1) was evaluated as a potential serum biomarker however was not reliably demonstrated in women with ectopic pregnancy. [12] In 2015, Zarezade et al, interrogated fallopian tubes of women with ectopic pregnancy, and the expression levels of vascular endothelial growth factor (VEGF) was found to be lower in women with ectopic pregnancies than the control group (women with normal fallopian tubes having benign hysterectomy). [13] In a similar vein Zou et al, investigated the presence of placental growth factor (PIGF) and found that there were no significant differences in PIGF levels in women with ectopic pregnancy or intrauterine pregnancy. [14] Current markers of endometrial function include leukemic inhibitory factor, glycodelin, mucin-1, and adrenomedullin and miRNAs. Specifically, miR-323-3p has been evaluated as possible serum biomarker for ectopic pregnancy. In 2012, Zhao et al, demonstrated that miR-323-3p was elevated in ECT compared to IUP, however the sensitivity was 37.0%. [15] Attention has continued to focus on the fallopian tube in an effort to find a potential biomarker for ectopic pregnancy. [4]

In a study by Vasquez et. al, biopsies of the fallopian tube were taken from 25 women with ECT, and they found that the proportion of ciliated cells were significantly lower than in women with normal intrauterine pregnancies. Samples were also taken from women prior to pregnancy with a history of tubal disease, and these women had deciliation found in their fallopian tubes. [16] This research has led to further evaluation of the fallopian tube, and the predisposition tubal damage may have for ECT. [17]

As demonstrated by the studies to date, a reliable diagnostic test for the accurate detection of early ectopic pregnancy is needed. A high precision biomarker classifier for this purpose is not currently available. Thus, this disclosure relates to the unexpected finding that the expression of a set of genes reliably classifies the location of a nonviable pregnancy as intrauterine or ectopic. Once biopsy expression levels for the gene set are established, samples can be classified by comparing to previously known expression level profiles of intrauterine and ectopic pregnancies. The classifier is adaptable to any platform, as the data demonstrates that expression level assay platforms achieved high levels of accuracy for pregnancy location classification (e.g., 91.1% and 87.9%). The inventors show that characterization of differing molecular profiles of abnormal early pregnancy can accurately and expeditiously simplify diagnosis and management.

The disclosure illustrates that a one-time analysis of gene expression levels in an endometrial biopsy specimen can be utilized to determine if a clinically non-viable pregnancy is intrauterine or ectopic. The advantages include diagnostic accuracy, expediency, efficiency, and time to therapeutic intervention. For example, the current clinical algorithm for vaginal bleeding or pain in the early first trimester pregnancy location consists of an ultrasound followed by serial human chorionic gonadotrophin (hCG) and possibly progesterone measurement. In contrast, the inventors have developed a method that requires only one clinical assessment for ectopic detection, thereby eliminating the need for serial visits.

Some current methods for diagnosing ectopic pregnancy consist of longitudinal observation with several marker tests as well physical observation of the pregnancy progress. This can result in delayed diagnosis and in some cases maternal fatality. The method disclosed herein avoids these problems by providing a clinical signature that correlates directly with ectopic pregnancy detection, which reduces false positive and false negative rates. The method can be performed on an endometrial biopsy specimen that is obtained by routine outpatient procedures.

Existing protocols for diagnosing and treating ectopic pregnancy include the use of quantitative HCG levels, ultrasound, intrauterine sampling, and administration of methotrexate (MTX). The inventors have developed a method for determining if an ectopic implantation exists with higher efficacy, which allows for further tailoring of the therapy (e.g. MTX) to safely treat this condition. Further, the inventors have developed a method to minimize the morbidity and mortality associated with delayed diagnosis of ectopic pregnancy by providing a single direct assay to accurately classify a nonviable pregnancy of unknown location (i.e. undetectable by transvaginal ultrasound) as intrauterine or ectopic.

In an aspect, the disclosure provides protocols to prospectively collect tissue and serum to bank for the identification of biomarker(s) to assist in the diagnosis of early pregnancy. In doing so, health care clinicians and providers may be better equipped to provide early identification of ectopic pregnancy, which may avoid a delay in diagnosis that can associate with maternal morbidity. In addition, the development of a reliable biomarker classifier may decrease the health care costs in the diagnosis and management of patients with all early abnormal pregnancies. FIG. 1 demonstrates a diagram outlining the steps taken to develop and validate a molecular marker(s) of early abnormal pregnancies.

The disclosure illustrates a discovery-based prospective cohort study which identifies a gene-classifier for the localization of early nonviable pregnancy as intrauterine versus ectopic. The inventors describe endometrial molecular signatures allowing for discovery of likely ectopic classifier candidates. Twelve out of 34 differentially expressed genes in the tested samples were categorized as cilia-associated. All 12 cilia-associated genes had increased expression in ECT in comparison to NV-IUP, and all 12 genes are known to have enriched expression in the fallopian tube (FIG. 2). Cilia are found throughout the human body, and function within the respiratory and reproductive tracts. Recent research indicates they may also play a role in nuclear-signaling. [31] Of the twelve cilia-associated genes studied, only one has been implicated in early pregnancy implantation. In 2015 Diao et al, demonstrated that deletion of LPAR3 in mice delayed embryo implantation due to delayed uterine receptivity. LPAR3 encodes the third G protein-coupled receptor for lysophosphatidic acid (LPA). [32] Lysophosphatidic acid receptors have been interrogated with respect to ovarian cancer risk. LPAR3, which the inventors have found to be increased in ECT, was shown by Si et al, to be increased in expression in patients with ovarian carcinoma. The sensitivity of this test was 97.9% in detecting ovarian carcinoma while the specificity was 98.5%. [33] Although not directly related to ectopic pregnancies, increased representation of cilia-associated genes potentially have a role in diagnosing abnormalities within the female reproductive tract. A comprehensive review of the literature has shown there is little that has been characterized regarding the remaining 11 cilia-associated genes.

Non-limiting examples of the genes comprising the classifier disclosed herein are cilia-associated genes that include Armadillo repeat containing 3 (ARMC3), Chromosome 20 open reading frame 85 (C20orf85), Cilia and flagella associated protein 47 (CFAP47), Cilia and flagella associated protein 126 (CFAP126), Dynein axonemal heavy chain 12 (DNAH12), Leucine rich repeat containing 46 (LRRC46), Lysophosphatidic acid receptor 3 (LPAR3), Radial spoke head component 4A (RSPH4A), Stomatin like 3 (STOML3), Tubulin polymerization promoting protein family member 3 (TPPP3), WD repeat domain 49 (WDR49) and Zinc finger B-box domain containing (ZBBX).

Armadillo repeat containing 3 (ARMC3) refers to a nucleic acid sequence, or fragment thereof, that has at least about 85%, 95%, or 100% identity to a representative sequence such as, for example, NCBI Accession No. NM_001282745, NM_001282746, NM_001282747 or NM_173081.

Chromosome 20 open reading frame 85 (C20orf85) refers to a nucleic acid sequence, or fragment thereof, that has at least about 85%, 95%, or 100% identity to a representative sequence, for example, NCBI Accession No. NM_178456.

Cilia and flagella associated protein 47 (CFAP47) refers to a nucleic acid sequence, or fragment thereof, that has at least about 85%, 95%, or 100% identity to a representative sequence, for example, NCBI Accession No. NM_001304548 or NM_152632.

Cilia and flagella associated protein 126 (CFAP126) refers to a nucleic acid sequence, or fragment thereof, that has at least about 85%, 95%, or 100% identity to a representative sequence, for example, NCBI Accession No. NM_001013625.

Dynein axonemal heavy chain 12 (DNAH12) refers to a nucleic acid sequence, or fragment thereof, that has at least about 85%, 95%, or 100% identity to a representative sequence, for example, NCBI Accession No. NM_001366028 or NM_198564.

Leucine rich repeat containing 46 (LRRC46) refers to a nucleic acid sequence, or fragment thereof, that has at least about 85%, 95%, or 100% identity to a representative sequence, for example, NCBI Accession No. NM_033413.

Lysophosphatidic acid receptor 3 (LPAR3) refers to a nucleic acid sequence, or fragment thereof, that has at least about 85%, 95%, or 100% identity to a representative sequence, for example, NCBI Accession No. NM_012152.

Radial spoke head component 4A (RSPH4A) refers to a nucleic acid sequence, or fragment thereof, that has at least about 85%, 95%, or 100% identity to a representative sequence, for example, NCBI Accession No. NM_001010892 or NM_001161664.

Stomatin like 3 (STOML3) refers to a nucleic acid sequence, or fragment thereof, that has at least about 85%, 95%, or 100% identity to a representative sequence, for example, NCBI Accession No. NM_001144033 or NM_145286.

Tubulin polymerization promoting protein family member 3 (TPPP3) refers to a nucleic acid sequence, or fragment thereof, that has at least about 85%, 95%, or 100% identity to a representative sequence, for example, NCBI Accession No. NM_015964 or NM_016140.

WD repeat domain 49 (WDR49) refers to a nucleic acid sequence, or fragment thereof, that has at least about 85%, 95%, or 100% identity to a representative sequence, for example, NCBI Accession No. NM_001348951, NM_001348952, NM_001366157 or NM_001366158.

Zinc finger B-box domain containing (ZBBX) refers to a nucleic acid sequence, or fragment thereof, that has at least about 85%, 95%, or 100% identity to a representative sequence, for example, NCBI Accession No. NM_001199201, NM_001199202, or NM_024687.

In one aspect, the disclosure provides a method for detecting ectopic pregnancy in a patient, comprising detecting in a biological sample from the patient, differential expression of at least one gene selected from ARMC3; C20orf85; CFAP47; CFAP126; DNAH12; LRRC46; LPAR3; RSPH4A; STOML3; TPPP3; WDR49; and ZBBX, or orthologs thereof, wherein the differential expression of the at least one gene is indicative of ectopic pregnancy.

In another aspect, the disclosure provides methods wherein the methods comprise detecting at least two, at least three, at least four, at least five, at least six, at least seven, at least eight, at least nine, at least ten, at least eleven or at least twelve mRNAs selected from ARMC3; C20orf85; CFAP47; CFAP126; DNAH12; LRRC46; LPAR3; RSPH4A; STOML3; TPPP3; WDR49; and ZBBX. In yet further embodiments, the methods comprise detecting ARMC3; C20orf85; CFAP47; CFAP126; DNAH12; LRRC46; LPAR3; RSPH4A; STOML3; TPPP3; WDR49; and ZBBX.

Endometrial biopsies were analyzed via microarray analysis to determine differentially expressed genes (DEG). Orthogonal validation of gene array results was conducted using quantitative real time PCR (qPCR). Polymerase chain reaction (PCR) is a relatively simple and highly prevalent molecular biology technique to amplify and detect DNA and RNA sequences. Quantitative PCR (qPCR) allows for real-time, sensitive, quantitative analysis of a sample. It is often used to detect DNA sequences when they are in low abundance in a sample or to quantify gene expression levels. In qPCR, DNA amplification is monitored at each cycle of PCR.

The pathogenesis of abnormal expression of these cilia-associated genes in ECT is unknown. The inventors postulate that abnormal implantation in the fallopian tube results in disruption of fallopian tube promoting up-regulation in ciliary gene expression or desquamation into the uterine endometrium. Alternatively, the ciliated cells themselves originating within the fallopian tube may be shed and migrate to the endometrium. Regardless of pathophysiology, this increased signal of cilia-associated genes demonstrates, with high accuracy, a molecular panel that differentiates ECT and NV-IUP by sampling the uterine endometrium in patients with early pregnancy failure.

Gestational age was noted to be statistically significant between the intrauterine pregnancy and ectopic pregnancy cohorts.

This finding was expected, as patients with ectopic pregnancy predictably present with symptoms of abnormal bleeding and pain which often prompt them to seek medical care earlier in her pregnancy. In the development of a biomarker to distinguish ectopic pregnancy from intrauterine pregnancy, the earlier clinical presentation of women with ectopic pregnancies has important implications. Women with ectopic pregnancy potentially may have lower levels of the substrates of interest, which may limit the detection.

A p-value of 0.10 and effect size (0.5 $\log_2$) was chosen as this study has relatively small sample size. This allowed for capture of signals that would not be detected as differentially expressed due to limitations with the small sample size. The study is also constrained by detection of endometrial markers in non-viable pregnancies, as viable pregnancies are not sampled due to the risk of disrupting a normal intrauterine pregnancy. However, this has limited impact on the study in distinguishing between ectopic pregnancies versus intrauterine pregnancies. Although the determination of abnormal pregnancy by definition is inclusive of many abnormalities that have the potential to skew the endometrial gene expression profiles due to the possibility of inclusion of an aneuploidy pregnancy, this confounder is present in the clinical situation in which one needs to differentiate these pregnancy types. Early pregnancies of unknown location are inclusive of all abnormal pregnancies, whether ectopic, aneuploid or abnormally implanted. Ultimately, development of a serum diagnostic that differentiates ectopic from viable intrauterine pregnancy (as early as possible) will assist with elucidating appropriate treatments.

As shown by the examples, this study illustrates consistent data sampling techniques for a homogenous tissue bank collection, characterization of demographic data, prospective diagnosis with comparative histologic verification as well as corresponding serum samples for each patient. This allows for the development of a serum biomarker for interrogation of both the endometrial tissue as well as expression in the maternal serum in future studies.

The observed enrichment of fallopian tube cilia-associated genes in the endometrium may uniquely represent the pathophysiological changes in ectopic pregnancy. The inventors have identified cilia-associated genes as a classifier for ectopic pregnancy with high accuracy for delineating ectopic from abnormal intrauterine pregnancies.

In one aspect, the disclosure provides a method for characterizing a pregnancy, the method comprising: detecting expression level of at least two, at least three, at least four, at least five, at least six, at least seven, at least eight, at least nine, at least ten, at least eleven or at least twelve mRNAs selected from ARMC3; C20orf85; CFAP47; CFAP126; DNAH12; LRRC46; LPAR3; RSPH4A; STOML3; TPPP3; WDR49; and ZBBX in a biological sample obtained from the patient; measuring the expression level of the at least one mRNA; and characterizing pregnancy as ectopic when the expression levels are increased. Thus the expression levels in the patient sample are higher than the mean and/or median expression level of the same mRNA in the reference sample.

In embodiments of the above aspect, the disclosure provides methods that comprise detecting expression of at least two, at least three, at least four, at least five, at least six, at least seven, at least eight, at least nine, at least ten, at least eleven or at least twelve mRNAs selected from ARMC3; C20orf85; CFAP47; CFAP126; DNAH12; LRRC46; LPAR3; RSPH4A; STOML3; TPPP3; WDR49; and ZBBX in a biological sample obtained from the subject. In some embodiments, the biological sample is an endometrial biopsy.

The methods disclosed herein comprise detection of biomarkers, (e.g., nucleic acids such as mRNA) and may include detection of the total number of counts for a particular marker or set of markers, detection of the mean marker, detection of a change in the mean marker, and/or detection of the median for a particular marker or set of markers, or detection of the presence of a particular marker or set of markers. Accordingly, in any of the aspects and embodiments disclosed herein, methods include detection of the presence, number, mean, median, or change in frequency of one or more of the markers (e.g., mRNA markers).

"Detect" refers to identifying the presence, absence or amount of the analyte to be detected, which in the various aspects and embodiments disclosed herein, comprises mRNA. As discussed herein the detection of mRNA markers (i.e., mRNAs from cilia-associated genes) can be used to assess the mean expression level, total expression level, and/or median expression level, in a patient.

In the methods disclosed herein, the detection may be performed on samples that are derived from a patient once, or at plurality of time points. For example, patient samples may be obtained during screening as initial diagnosis, and immediately prior to any treatment or therapeutic intervention.

In some embodiments and aspects disclosed herein, the methods may comprise therapeutic intervention for a patient identified as having an ectopic pregnancy. In such embodiments any therapeutic method generally known in the art may be recommended by the patient's physician. Examples include expectant management, medical management with methotrexate, or surgery. In some embodiments expectant management may be appropriate only when beta hCG levels are low and declining. In some embodiments surgical treatment may be appropriate if ruptured ectopic pregnancy is suspected and if the patient is hemodynamically unstable.

Some aspects and embodiments of the disclosure are illustrated by the following examples. These examples are provided to describe specific embodiments of the technology and do not limit the scope of the disclosure. It will be understood by those skilled in the art that the full scope of the disclosure is defined by the claims appending this specification, and any alterations, modifications, or equivalents of those claims.

EXAMPLES

Example 1. Creation of Biorepository and Patient Characteristics

The following study compares transcriptome profiles from women with ectopic pregnancy (ECT) or abnormal intrauterine pregnancy (AIUP). Adult females ages 18-45 years old clinically diagnosed with a nonviable first trimester pregnancy, ectopic pregnancy, or pregnancy of undetermined location scheduled for surgery or an in-office procedure (manual vacuum aspiration) to address the clinically diagnosed nonviable pregnancy were included in the study. The patients were required to be hemodynamically stable and competent to provide consent in order to participate. Patients were excluded if they were hemodynamically unstable, had suspicion or known molar pregnancy or an intrauterine device in place.

Subjects meeting inclusion criteria voluntarily enrolled prior to their scheduled procedure. On the day of the scheduled procedure, participants had a vial of blood (approximately 5 cc total) drawn at the time of intravenous line (IV) placement or at the laboratory. Endometrial sampling was performed. The endometrial tissue was rinsed in PBS (phosphate buffered solution), and divided into several equal portions. A portion was snap frozen in liquid nitrogen. The remaining portion was transferred to a 10% formaldehyde solution and sent to pathology for histologic analysis. Blood samples were processed, and a portion of the blood specimen processed to plasma and stored at −80° C. The scheduled procedure (dilation and curettage/MVA and/or laparoscopy) was then completed as planned.

If patients were scheduled to have laparoscopy due to suspected ectopic pregnancy, and the decision was made to perform salpingectomy by the operating surgeon to treat the ectopic pregnancy, the fallopian tube was removed intact from the body in an expeditious fashion. Intraoperative dissection of the specimen was performed using a dissecting microscope. The trophoblastic-tubal interface was isolated and dissected from the sample, and was snap frozen in liquid nitrogen. The sample was stored at −80° C. A portion of the remaining tubal tissue was snap frozen in liquid nitrogen and stored at −80° C., and the remaining tissue was sent to pathology for analysis in formaldehyde.

Endometrial biopsies were collected from 69 women with non-viable pregnancies undergoing surgical or manual vacuum aspiration intervention with estimated gestational ages ranging from 37 to 65 days. From this biorepository, nine samples from women with NV-IUP and eight from women with ECT were selected for microarray analysis using the Affymetrix Human Gene 2.0 ST Array. Linear Models for Microarray Data (limma) was used to determine differentially expressed genes (DEG). Predictive modeling was performed on cilia-associated DEG using the k-nearest neighbors (KNN) algorithm with repeated 10-fold cross-validation. Orthogonal validation of gene array results was conducted using quantitative real time PCR.

Patient Characteristics: At total of 43 patients were enrolled in this study from October 2013 through January 2016. Of the 43 patients enrolled, 17 of the samples were noted to be high-quality with known patient demographics, and adequate tissue amounts to proceed with analysis (FIG. 3). Gestational age was noted to be significantly different between the cohorts of patients. The mean gestational age with NV-IUP was 58.6 days and 44.8 days with ECT (CI 7.0, ±20.0, $p<0.05$). Patients with ectopic pregnancies underwent surgical treatment on average 45.9 days gestational age, whereas those with abnormal intrauterine pregnancies underwent surgical management almost 2 weeks later, an average gestational age of 58.5 days. This is expected, as patients with ectopic pregnancies typically have symptoms of abnormal vaginal bleeding, and abdominal pain which leads them to seek medical care sooner than those with an intrauterine gestation.

Example 2. Microarray Analysis

The snap frozen samples of the endometrial tissues were then processed for RNA isolation. The integrity of RNA samples was assessed with an Agilent 2100 Bioanalyzer (Agilent Technologies Inc., Santa Clara, CA). Processing of the RNA samples that passed quality control was performed according to the standard Affymetrix GeneChipWhole Transcript Sense Target labeling protocol. The arrays were then scanned with an Affymetrix GeneChip13000 scanner. Image generation and feature extraction were performed using Affymetrix GeneChip Command Console Software. [18] Microarray results will be made publicly available through NCBI's Gene Expression Omnibus (GEO). [19][20]

Example 3. Bioinformatics and Statistical Analyses

Microarray intensities were background corrected, $\log_2$ transformed, and quantile normalized by Robust Multi-array Average (RMA) using R package oligo. [21][22] Differential expression was determined by linear modeling of results with limma. [23] Genes were identified as differentially expressed if they had false discovery rate (FDR) adjusted p-values of at most 0.1 and at least a 0.5 $\log_2$ fold-change.

To classify data as either NV-IUP or ECT, one hundred repetitions of 10-fold cross-validation (CV) using k-Nearest Neighbor (KNN) models were performed with k chosen based on optimal accuracy. R packages caret and class were used for CV and machine learning. [24][25] ROC curves were generated for each repetition with ROCR, and the average accuracy and area under the ROC curve (AUROC) were calculated. [26] Mann-Whitney U Test and Student's t-test were used to determine statistical significance. All analyses were performed with R (3.3.2).

Example 4. Experimental Validation

The RNA from the same tissue samples that underwent microarray analysis then underwent qPCR analysis. Unique primers and probes were designed online from Roche Diagnostics, Mannheim, Germany (FIG. 4). RNA was reverse-transcribed and replicated simultaneously using the LC480 RNA Master Hydrolysis Probe kit. Real-time PCR reactions were performed in a 12 μl reaction volume comprised of 0.5 μM of each gene-specific primer and probe at 0.25 μM. Reactions occurred with the following protocol: 30 min at 63° C., Denaturation-1 sec at 95° C., Amplification (3 step) 10 sec at 95° C., 1 min at 58° C., 10 sec at 72° C., cooling 30 sec at 40° C. per the RT-PCR program on the Roche Lightcycler 480 II protocol (Roche Molecular Systems, Indianapolis, IN). The amount of RNA used ranged from 200 ng for RPL19 (housekeeping gene) to 600 ng for the PUL genes. All samples were run in triplicate.

Example 5. Gene Expression Results Show Unsupervised Clustering of Samples Based on Non-Viable Pregnancy Location A total of 44,629 transcripts were analyzed with the Affymetrix GeneChip Human Gene 2.0 ST Array. Differential expression analysis revealed 34 differentially expressed genes (DEG). For the 34 DEG, ECT values ranged from 0.15 to 2.93 times the expression in NV-IUP with adjusted p-values of 0.059 to 0.097 (FIG. 5). An increase in ECT gene expression was seen in 21 of the 34 DEG, while 13 genes showed a decrease in expression.

Figure 6:
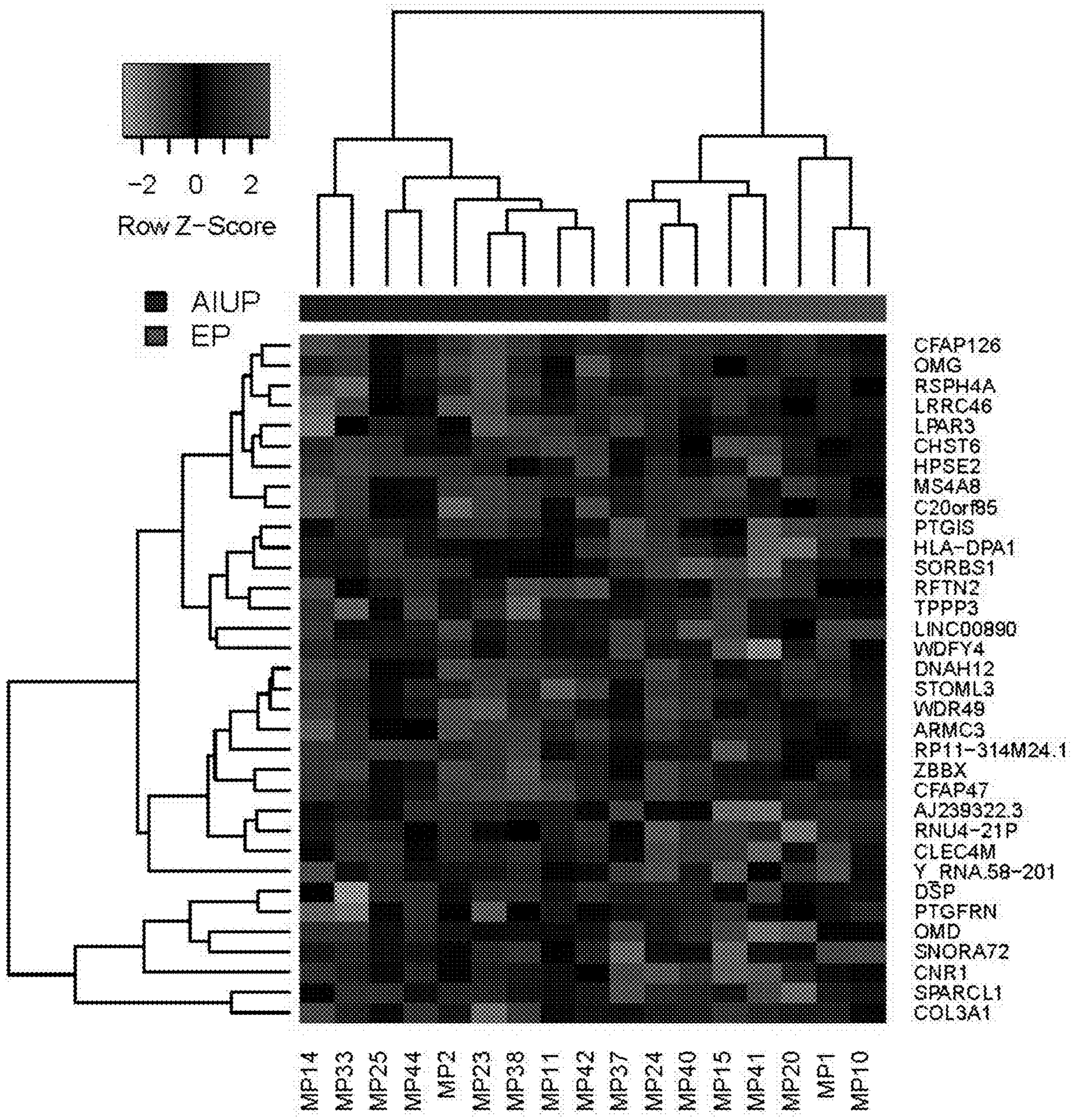
FIG. 6 depicts hierarchical clustering of gene expression results from the 34 differentially expressed genes identified with linear models for microarray data (limma). Unsupervised clustering resulted in the separation of samples by pregnancy location. Dendrograms show Euclidean distance between clusters with average linkage. The corresponding heatmap represents microarray expression results for each gene with green for low and red for high expression.

A separation of ECT from NV-IUP was achieved through hierarchical clustering based on gene expression of the 34 DEG (FIG. 6). ECT was successfully distinguished from NV-IUP with the largest distance being between ECT and NV-IUP clusters revealing similarity in gene expression within groups rather than between groups based on the differentially expressed genes identified.

Example 6. Cilia-Associated Genes are Enriched in Endometrial Biopsies from Women with Ectopic Pregnancy Pathway and functional analysis was initially performed with Ingenuity Pathway Analysis (Qiagen, Redwood City, CA) and DAVID 6.8. [27][28] Results were uninformative with at most 1 gene enriched in pathways if significant enrichment was found. Upon review of the DEG list, it was noted that several genes were not well characterized and many had unknown function. After reviewing all genes in the Human Protein Atlas (HPA), a trend of association with cilia was identified.[29] The cilia structure is known to be affected by ectopic pregnancy and was considered a structure of interest.

In 2012, Ivliev et al., performed an in silico co-expression network study comparing tissues with ciliated cells and gene expression levels resulting in a comprehensive list of cilia-associated genes. [30] This cilia-associated gene list was compared to the generated DEG list and a significant overlap was found between the two (Fisher's exact test p<0.0001). Twelve out of the 34 differentially expressed genes were categorized as cilia-associated, specifically ARMC3; C20orf85; CFAP47; CFAP126; DNAH12; LRRC46; LPAR3; RSPH4A; STOML3; TPPP3; WDR49; and ZBBX. In addition, all 12 genes had increased expression in ECT in comparison to NV-IUP, and all 12 genes are known to have enriched expression in the fallopian tube (FIG. 2). These 12 gene features were selected for additional analysis as potential diagnostic predictors based on the biological relevance of a disrupted fallopian tube in ECT.

Figure 7:
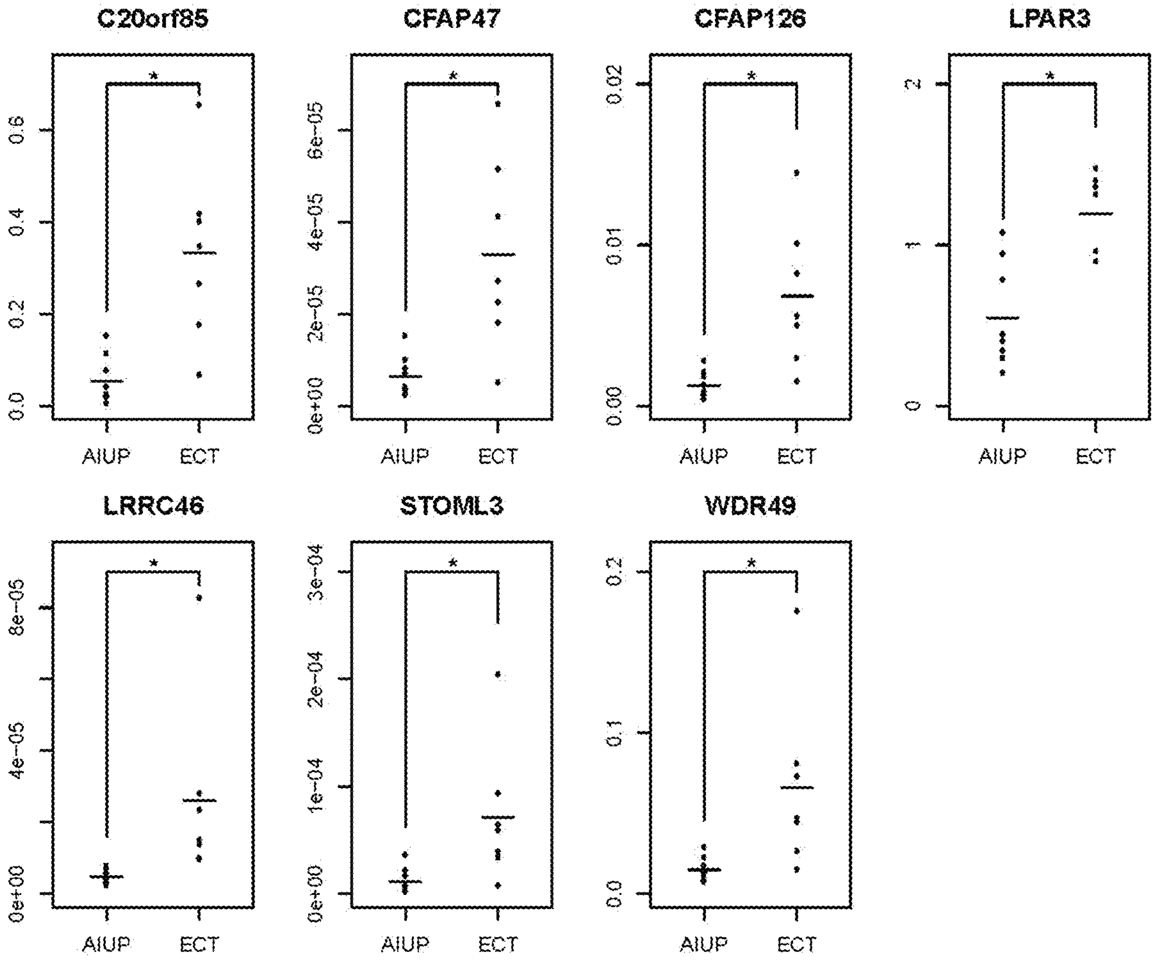
FIG. 7 illustrates validation of gene expression results with qPCR. Seven cilia-associated differentially expressed genes (C20orf85; CFAP47; CFAP126; LPAR3; LRRC46; STOML3; and WDR49) were confirmed to have statistically significant ($p<0.05$) increased expression in ectopic pregnancy when compared to non-viable intrauterine pregnancy biopsies. Results are presented relative to RPL19 expression in all samples.

Example 7. An Increase in Expression of Cilia-Associated Genes was Validated in Ectopic Pregnancy Biopsies To validate this up-regulation of cilia-associated genes, qPCR was performed to confirm gene expression of 7 out of the 12 cilia-associated genes of interest. All 7 genes profiled confirmed upregulation in ECT when compared to NV-IUP biopsy responses, in agreement with microarray results (FIG. 7). Increased expression of cilia-associated genes were statistically significant and resulted in ECT mean fold-changes ranging from 2.2 to 6.3 relative to NV-IUP with C20orf85 having the most significant difference between ECT and NV-IUP samples.

Figure 8:
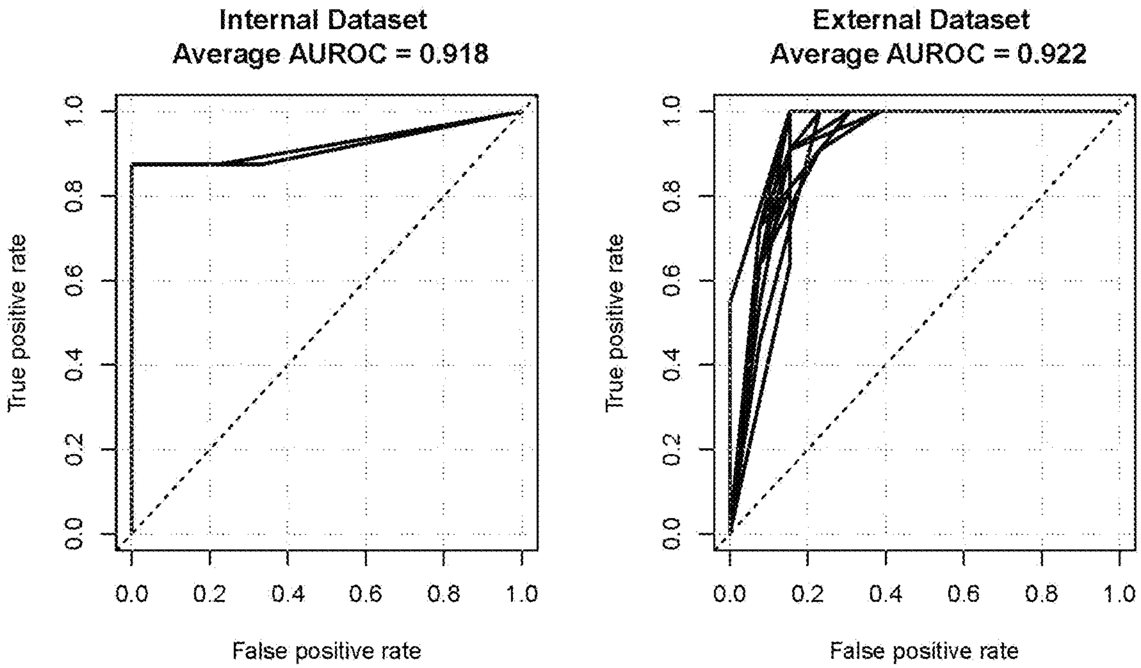
FIG. 8 depicts receiver operating characteristic (ROC) curves for 100 repetitions of 10-fold cross-validation of cilia-associated gene classifier predicting non-viable pregnancy location with internal (n=17) and external (n=24) gene expression results. Average area under ROC curves were 0.918 and 0.922, respectively for the internal and external dataset showing reliable pregnancy location with the cilia-associated gene classifier.
Figure 9A:
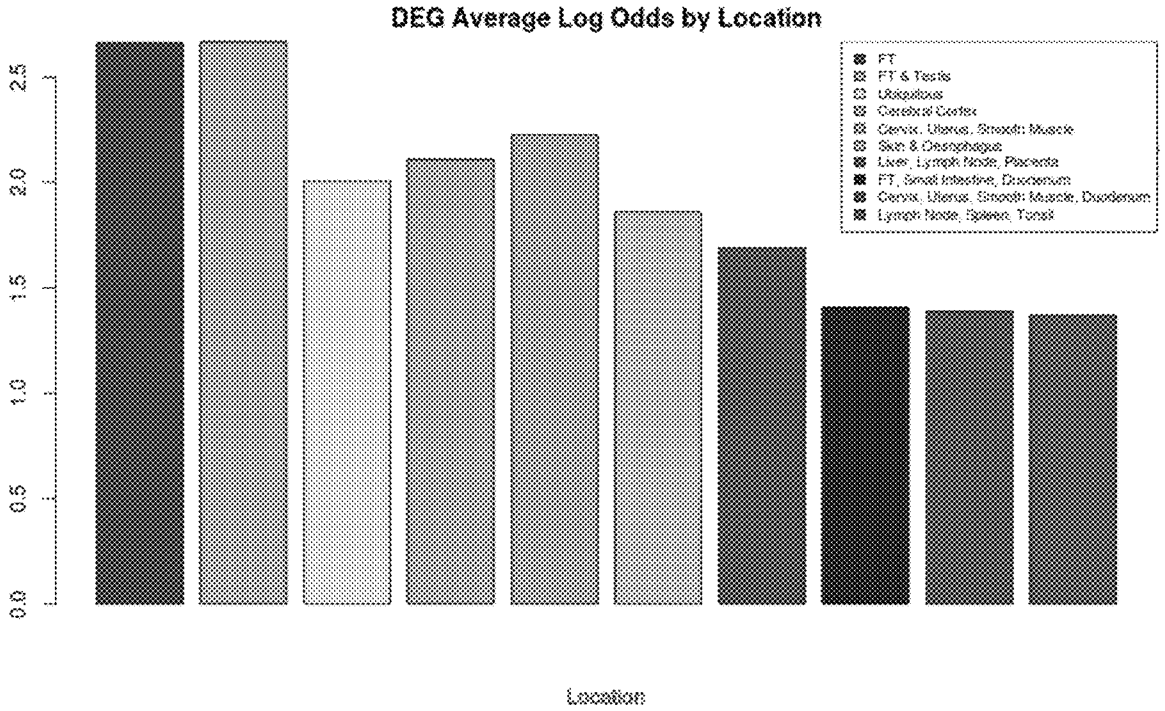
FIGS. 9A & 9B show gene expression and tissue expression patterns initially produced leading to the discovery of the cilia-associated gene enrichment.
Figure 9B:
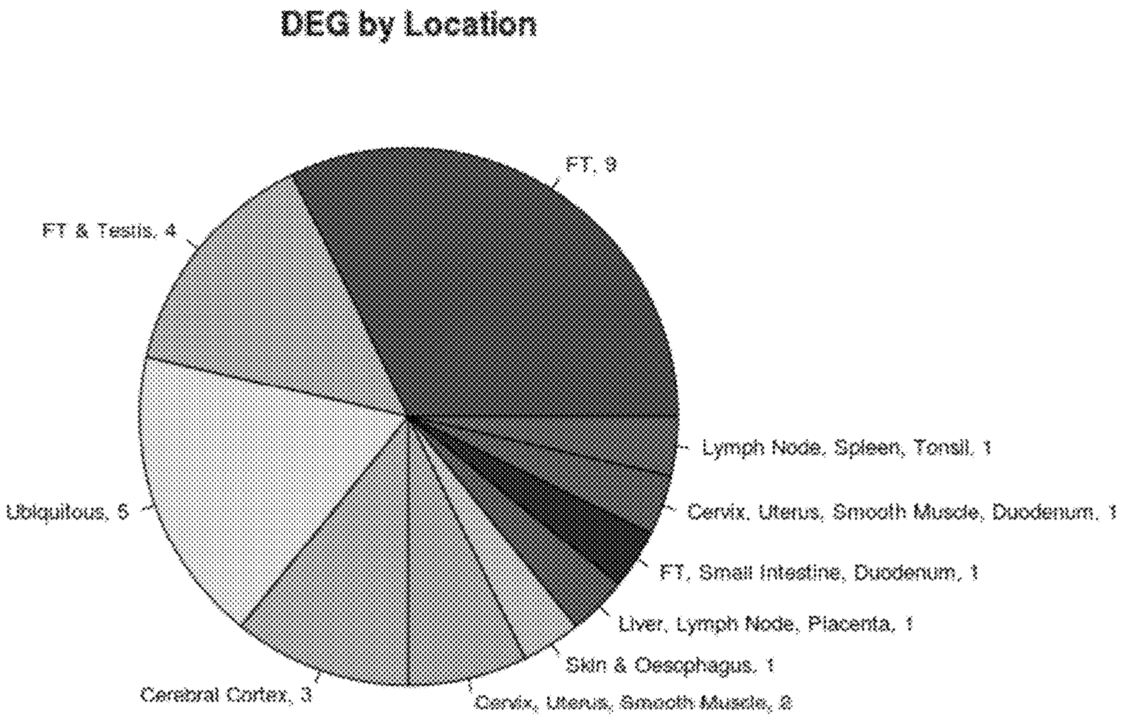

Example 8. Twelve Cilia-Associated Genes Successfully Classify Location of Non-Viable Pregnancies To assess the feasibility of determining non-viable pregnancy location based on the 12 cilia-associated gene classifier, KNN predictive modeling was used with 10-fold cross-validation (CV) on the internal dataset (n=17). Based on model classification and receiver operating characteristic (ROC) curves, this 12 gene classifier is able to successfully predict non-viable pregnancy location with accuracy of 91.1% and AUROC of 0.918 averaged over 100 repetitions of 10-fold CV (FIG. 8).

An external dataset was used to assess the predictive capability of the 12 cilia-associated gene classifier to determine pregnancy location. In 2011, Duncan et al., analyzed decidualization matched endometrial biopsies (n=24) from women undergoing surgical termination of a viable intrauterine pregnancy and women with ectopic pregnancies using the Affymetrix Human Genome U133 Plus 2.0 Array. [1] The classification procedure was repeated on the external dataset resulting in similar predictability with an average AUROC of 0.922 and average accuracy of 87.9% (FIG. 8). These results confirm the successful classification of pregnancy location with the 12 gene classifier on an external dataset, thus providing validation of the results using a different microarray platform. This provides compelling evidence that these genes are naturally upregulated in ECT pregnancy. Additionally, this external validation confirmed the gene set could be used with other gene expression platforms and is not specific to the measurement method.

Example 9: Results

Comparison of ECT versus NV-IUP samples identified 28 endometrial DEG. Fisher exact test revealed a statistically significant (p<0.0001) enrichment of cilia-associated genes. All 12 cilia-associated genes were upregulated in ECT samples and have been previously demonstrated to be highly expressed in human Fallopian tube. qPCR validation confirmed gene expression results with 7 of 7 genes tested having statistically significant (p<0.05) upregulation in ECT versus NV-IUP samples (>2 fold). Based on KNN predictive classification, an average accuracy of 91.1% for the detection of ectopic pregnancy was achieved using a classifier consisting of these 12 cilia-associated genes. This data was cross-validated with an external data set and this analysis revealed 87.9% average accuracy in detecting ectopic pregnancy, with an average area under the receiver operator characteristic curve (AUROC) of 0.922. [1].

Example 10: Further Validation

Further validation of the gene classifier for use in diagnosis of ectopic pregnancy was performed on another data set. Quantitative PCR was carried out for orthogonal validation using 36 specimens (20 intrauterine miscarriages v. 16 surgically confirmed ectopic pregnancies). This dataset validated statistically significant (P<0.05) increased expression for 10 of the 12 genes on the classifier. For one gene (LPAR3), the qPCR could not be optimized and for another gene (STOML3), increased expression consistent with array result was observed, but was not statistically significant (P=0.18). In aggregate, these results orthogonally confirm the validity of the classifier for delineation of ectopic in the setting of NVPUL.

The nCounter® platform was used to perform multiplex analysis. The results confirmed significant differential expression, with increased expression in ectopic pregnancy as compared to abnormal IUP for 10 of 12 genes in the endometrial NVPUL classifier. CFAP126 and STOML3 were the exceptions, despite CFAP126 demonstrating consistent differential expression on quantitative PCR. These results provide orthogonal validation of array results by two separate interrogative methods and confirm the authenticity of the findings.

INCORPORATION BY REFERENCE

All publications and patents mentioned herein are hereby incorporated by reference in their entirety as if each individual publication or patent was specifically and individually indicated to be incorporated by reference.

While specific aspects of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

REFERENCES

1. Duncan, W. C., et al., *Ectopic pregnancy as a model to identify endometrial genes and signaling pathways important in decidualization and regulated by local trophoblast*. PLoS One, 2011. 6(8): p. e23595.
2. Tong, S., M. M. Skubisz, and A. W. Horne, *Molecular diagnostics and therapeutics for ectopic pregnancy*. Mol Hum Reprod, 2015. 21(2): p. 126-35.
3. Kirk, E., C. Bottomley, and T. Bourne, *Diagnosing ectopic pregnancy and current concepts in the management of pregnancy of unknown location*. Hum Reprod Update, 2014. 20(2): p. 250-61.
4. Senapati, S. and K T Barnhart, *Biomarkers for ectopic pregnancy and pregnancy of unknown location*. Fertil Steril, 2013. 99(4): p. 1107-16.
5. Barnhart, K. T., et al., *Symptomatic patients with an early viable intrauterine pregnancy: HCG curves redefined*. Obstet Gynecol, 2004. 104(1): p. 50-5.
6. Seeber, B. E., et al., *Application of redefined human chorionic gonadotropin curves for the diagnosis of women at risk for ectopic pregnancy*. Fertil Steril, 2006. 86(2): p. 454-9.
7. Condous, G., et al., *Prediction of ectopic pregnancy in women with a pregnancy of unknown location*. Ultrasound Obstet Gynecol, 2007. 29(6): p. 680-7.
8. Silva, C., et al., *Human chorionic gonadotropin profile for women with ectopic pregnancy*. Obstet Gynecol, 2006. 107(3): p. 605-10.
9. Kirk, E., et al., *The diagnostic effectiveness of an initial transvaginal scan in detecting ectopic pregnancy*. Hum Reprod, 2007. 22(11): p. 2824-8.
10. Takacs, P., et al., *Placental mRNA in maternal plasma as a predictor of ectopic pregnancy*. Int J Gynaecol Obstet, 2012. 117(2): p. 131-3.
11. Home, A. W., et al., *Evaluation of ADAM-12 as a diagnostic biomarker of ectopic pregnancy in women with a pregnancy of unknown location*. PLoS One, 2012. 7(8): p. e41442.
12. Tornehave, D., et al., *Placental proteins in peripheral blood and tissues of ectopic pregnancies*. Gynecol Obstet Invest, 1987. 23(2): p. 97-102.
13. Zarezade, N., et al., *mRNA expression of VEGF and its receptors in fallopian tubes of women with ectopic pregnancies*. Int J Fertil Steril, 2015. 9(1): p. 55-64.
14. Zou, S., et al., *Comparison of the diagnostic values of circulating steroid hormones, VEGF-A, PIGF, and ADAM12 in women with ectopic pregnancy*. J Transl Med, 2013. 11: p. 44.
15. Zhao, Z., et al., *Circulating microRNA miR-323-3p as a biomarker of ectopic pregnancy*. Clin Chem, 2012. 58(5): p. 896-905.
16. Vasquez, G., R. M. Winston, and I. A. Brosens, *Tubal mucosa and ectopic pregnancy*. Br J Obstet Gynaecol, 1983. 90(5): p. 468-74.
17. Lyons, R. A., E. Saridogan, and O. Djahanbakhch, *The reproductive significance of human Fallopian tube cilia*. Hum Reprod Update, 2006. 12(4): p. 363-72.
18. Vleeshouwer-Neumann, T., et al., *Histone Deacetylase Inhibitors Antagonize Distinct Pathways to Suppress Tumorigenesis of Embryonal Rhabdomyosarcoma*. PLoS One, 2015. 10(12): p. e0144320.
19. Edgar, R., M. Domrachev, and A. E. Lash, *Gene Expression Omnibus: NCBI gene expression and hybridization array data repository*. Nucleic Acids Res, 2002. 30(1): p. 207-10.
20. Barrett T, W. S., Ledoux P, Evangelista C, Kim I F, Tomashevsky M, Marshal K A, Phillippy K H, Sherman P M, Holko M, Yefanov A, Lee H, Zhang N, Robertson C L, Serova N, David S, Soboleva A, *NCBI GEO: archive for functional genomics data sets-update*. Nucleic Acids Res, 2013. 41: p. D991-5.
21. Rafael A. Irizarry, B. H., Francois Collin, Yasmin D. Beazer-Barclay, Kristen J. Antonellis, Uwe Scherf, Terence P. Speed, *Exploration, normalization and summaries of high density oligonucleotide array probe level data*. Biostatistics, 2003. 4(2): p. 249-264.
22. Carvalho, B. S. and R. A. Irizarry, *A framework for oligonucleotide microarray preprocessing*. Bioinformatics, 2010. 26(19): p. 2363-7.
23. Ritchie, M. E., et al., *limma powers differential expression analyses for RNA-sequencing and microarray studies*. Nucleic Acids Res, 2015. 43(7): p. e47.
24. Kuhn, M., *Caret package*. Journal of Statistical Software, 2008. 28(5).
25. Venables, W., Ripley B D, *Modern Applied Statistics*. 2002. Fourth Edition.
26. Sing, T., et al., *ROCR: visualizing classifier performance in R*. Bioinformatics, 2005. 21(20): p. 3940-1.
27. Huang, D. S. B. L. R., *Systematic and integrative analysis of large gene lists using DAVID Bioinformatics Resources*. Nature Protoc, 2009. 4(1): p. 44-57.
28. Huang, D. S. B. L. R., *Bioinformatics enrichment tools: paths toward the comprehensive functional analysis of large gene lists*. Nucleic Acids Research, 2009. 37(1): p. 1-13.
29. Uhlen, M., et al., Proteomics. *Tissue-based map of the human proteome*. Science, 2015. 347(6220): p. 1260419.
30. Ivliev A E, t. H. P., van Roon-Mom M V C, Peters D J M, Sergeeva M G, *Exploring the Transcriptome of Ciliated Cells Using In Silico Dissection of Human Tissues*. PLoS ONE, 2012. 7(4): p. e356618.
31. McClure-Begley, T. D. and M. W. Klymkowsky, *Nuclear roles for cilia-associated proteins*. Cilia, 2017. 6: p. 8.
32. Diao, H., et al., *Deletion of Lysophosphatidic Acid Receptor 3 (Lpar3) Disrupts Fine Local Balance of Progesterone and Estrogen Signaling in Mouse Uterus During Implantation*. Biol Reprod, 2015. 93(5): p. 123.
33. Si, J., et al., *Expressions of lysophosphatidic acid receptors in the development of human ovarian carcinoma*. Int J Clin Exp Med, 2015. 8(10): p. 17880-90.

We claim:

1. A method of treating an ectopic pregnancy in a patient comprising: obtaining results of an applied k-Nearest Neighbor (KNN) algorithm on mRNA expression levels of a set of biomarkers in a biological sample obtained from the patient, wherein the applied KNN algorithm was trained on expression data obtained from historical patient samples having ectopic or intrauterine pregnancies for the set of biomarkers consisting of: ARMC3, C20orf85, CFAP47, CFAP126, DNAH12, LRRC46, LPAR3, RSPH4A, STOML3, TPPP3, WDR49, and ZBBX, and optionally further consisting of at least one of: AJ239322.3, CHST6, CLEC4M, CNR1, COL3A1, DSP, HLA-DPA1, HPSE2, LINC00890, MS4A8, OMD, OMG, PTGERN, PTGIS, FRFTN2, RNU4-21P, RP11-314M24.1, SNORA72, SORBS1, SPARCL1, WDFY4, and Y RNA.58-201; and wherein the results indicate that the patient has an ectopic pregnancy and not a normal or abnormal intrauterine pregnancy; and treating the patient with methotrexate or by surgery.

2. The method of claim 1, wherein the patient is diagnosed with an early-stage ectopic pregnancy.

3. The method of claim 1, wherein the patient is in the first trimester of pregnancy.

4. The method of claim 1, wherein the abnormal intrauterine pregnancy is selected from the group consisting of a pregnancy of unknown location (PUL), a non-viable pregnancy of unknown location (NV-PUL), and a non-viable intrauterine pregnancy (NV-IUP).

5. The method of claim 1, wherein the method further comprises performing a transvaginal ultrasound (TVUS), detecting serum human chorionic gonadotropin (hCG), or both.

6. The method of claim 1, wherein mRNA expression levels is measured using a binding agent to one of each biomarker in the set of biomarkers.

7. The method of claim 6, wherein the binding agent is a polynucleotide capable of hybridizing to one of each biomarker in the set of biomarkers.

8. The method of claim 7, wherein the polynucleotide is labeled.

9. The method of claim 8, wherein the label is indirectly linked to the polynucleotide.

10. The method of claim 8, wherein the label comprises biotin.

11. The method of claim 10, wherein the biotin is bound to a streptavidin-conjugated phycoerythrin (SAPE).

12. The method of claim 7, wherein the polynucleotide is immobilized on a microarray.

13. The method of claim 7, wherein the polynucleotide further comprises a capture probe.

14. The method of claim 7, wherein the set of biomarkers further consists of at least one of: AJ239322.3, CHST6, CLEC4M, CNR1, COL3A1, DSP, HLA-DPA1, HPSE2, LINC00890, MS4A8, OMD, OMG, PTGFRN, PTGIS, FRFTN2, RNU4-21P, RP11-314M24.1, SNORA72, SORBS1, SPARCL1, WDFY4, and Y RNA.58-201.

15. The method of claim 6, wherein the binding agent is a polypeptide capable of binding to one of each biomarker in the set of biomarkers.

16. The method of claim 15, wherein the polypeptide is labeled.

17. The method of claim 16, wherein the label is indirectly linked to the polypeptide.

18. The method of claim 16, wherein the label comprises biotin.

19. The method of claim 18, wherein the biotin is bound to a streptavidin-conjugated phycoerythrin (SAPE).

20. The method of claim 15, wherein the polypeptide is immobilized on a microarray.

21. The method of claim 15, wherein the polypeptide further comprises a capture probe.

22. The method of claim 15, wherein the set of biomarkers further consists of at least one of: AJ239322.3, CHST6, CLEC4M, CNR1, COL3A1, DSP, HLA-DPA1, HPSE2, LINC00890, MS4A8, OMD, OMG, PTGFRN, PTGIS, FRFTN2, RNU4-21P, RP11-314M24.1, SNORA72, SORBS1, SPARCL1, WDFY4, and Y RNA.58-201.

* * * * *